United States Patent [19]

Griffith et al.

[11] Patent Number: 4,721,615
[45] Date of Patent: Jan. 26, 1988

[54] CALCIUM PHOSPHATES

[75] Inventors: Edward J. Griffith, Manchester; William C. McDaniel, St. Louis, both of Mo.

[73] Assignee: Monsanto Company, St. Louis, Mo.

[21] Appl. No.: 871,341

[22] Filed: Jun. 6, 1986

Related U.S. Application Data

[60] Division of Ser. No. 861,615, May 5, 1986, abandoned, which is a continuation of Ser. No. 567,720, Jan. 3, 1984, abandoned.

[51] Int. Cl.$^4$ .............................................. C01B 25/32
[52] U.S. Cl. ..................................... 424/57; 423/305; 423/308; 423/309
[58] Field of Search .................. 424/57; 423/308, 309, 423/305

[56] References Cited

U.S. PATENT DOCUMENTS

| 2,272,617 | 2/1942 | Cox et al. | 424/57 |
|---|---|---|---|
| 2,901,400 | 8/1959 | Thomas | 424/57 |
| 3,012,852 | 12/1961 | Nelson | 424/57 |
| 3,112,247 | 11/1963 | Schweizer | 424/57 |
| 3,334,979 | 8/1967 | Saunders et al. | 424/57 |
| 3,635,660 | 1/1972 | Bruce et al. | 23/108 |
| 3,829,562 | 8/1974 | Kim et al. | 424/57 |
| 3,885,029 | 5/1975 | Norfleet et al. | 424/57 |
| 4,044,105 | 8/1977 | Enomoto et al. | 423/308 |
| 4,203,955 | 5/1980 | Enomoto et al. | 423/308 |
| 4,312,843 | 1/1982 | Monty et al. | 423/309 |
| 4,472,365 | 9/1984 | Michel | 423/309 |
| 4,487,749 | 12/1984 | Sherif et al. | 423/309 |
| 4,587,120 | 5/1986 | Ozawa et al. | 424/57 |

FOREIGN PATENT DOCUMENTS

| 637092 | 9/1963 | Belgium | 424/57 |
|---|---|---|---|
| 673681 | 11/1963 | Canada | 423/308 |
| 36597 | 11/1970 | Japan | 424/57 |

Primary Examiner—John Doll
Assistant Examiner—Wayne A. Langel
Attorney, Agent, or Firm—R. Loyer

[57] ABSTRACT

Novel processes are provided for producing anhydrous dicalcium phosphate (DCPA) and the gamma and beta forms of calcium pyrophosphate (CPP) from the reaction of phosphoric acid and lime. Dentifrice compositions containing the resultant phosphates are also disclosed.

37 Claims, 3 Drawing Figures

300 X
⊣⊢
10 μm

756 X
⊣⊢
10 μm

CALCIUM PHOSPHATES

This is a division of application Ser. No. 861,615, filed May 5, 1986, which is a continuation of Ser. No. 567,720, filed Jan. 3, 1984, now abandoned.

This invention relates to improvements in the production of calcium phosphates, for example, anhydrous dicalcium phosphate, and the $\gamma$ and $\beta$ forms of calcium pyrophosphate and the use of such phosphates in dentifrice compositions. In particular, the calcium phosphate processes and products of this invention are based on the order of addition of the reactants used, namely phosphoric acid and lime, and that unique results (in processing and in the products obtained) are realized by adding phosphoric acid to a lime slurry which is the reverse order of addition employed in commercial practice.

BACKGROUND OF THE INVENTION

In making anhydrous dicalcium phosphate (hereafter DCPA) by prior art processes, several alternatives have been followed. In one process (Process I) and aqueous lime slurry is added to an aqueous phosphoric acid solution to form hydrated dicalcium phosphate or dicalcium phosphate dihydrate (hereafter DCPD) which is separated from the aqueous liquid phase and then dehydrated by heating. In another process, (Process II) a soluble salt of phosphoric acid, such as diammonium phosphate, and a soluble calcium salt, such as calcium chloride, are mixed together in aqueous solution to from hydrated dicalcium phosphate under acidic conditions. The resulting aqueous medium is then heated near 100° C. for a period of time sufficient to convert the dicalcium phosphate to the anhydrous form. This product is then separated from the aqueous medium and dried.

A process similar to Process II is used to produce anhydrous calcium hydrogen phosphate as in U.S. Pat. No. 3,635,860 to Joseph A. G. Bruce et al, issued Jan. 18, 1972. In accordance with this patent the anhydrous product can be converted to a calcium pyrophosphate by heating to about 500°–600° C. and this product can be used to produce luminescent phosphors.

The DCPA produced in accordance with Process I can be converted to a calcium pyrophosphate (CPP) which contains at least 70% of $\beta$ phase material by calcination at a temperature of about 700° C. However, when such calcination is carried out in commercial scale equipment, the CPP obtained will vary in properties from batch to batch and may not always be suitable as a dentifrice abrasive material. Thus such a material, in order to be commercially acceptable, should have good cleaning power, relatively low radioactive dentine enamel abrasion (RDA), high sodium fluoride compatibility, and stannous (tin) compatibility, resulting in a relatively low RDA to stannous compatibility ratio. If the products produced do not have such properties consistently the cost of acceptable product is obviously going to be greater than it would be if acceptable product could be produced consistently. The reason for variance in CPP properties from batch to batch are not clearly understood, but are believed to be influenced by crystal qualities (including crystal size), conditions of dehydration and conditions existing during the conversion of DCPA to CPP.

The applicants have found that the vital dentifrice abrasive properties of CPP can be controlled more consistently than has been possible heretofore in commercial practice if hydrated dicalcium phosphate is first formed by adding an aqueous phosphoric acid solution to an aqueous lime CaO or Ca(OH)$_2$ slurry with adequate agitation and holding the resultant product in an aqueous medium under elevated temperature conditions sufficient to dehydrate the dicalcium phosphate in such medium and form DCPA. This product can be used per se as a dentifrice polishing agent or it can be converted by calcination to the $\gamma$ or $\beta$ form of CPP depending on the calcination temperatures used. The $\beta$ form of CPP produced by the present process is substantially consistently useful as a polishing agent (or abrasive) in dentifrice compositions.

It can be seen from the foregoing that the present process differs from Process I, supra, primarily in the manner of mixing phosphoric acid and lime slurry to produce hydrated DCP and DCPA. The consequence of this difference will be apparent from the subsequent disclosure. One of the essential differences between the present processes and Process II is the starting materials employed to prepare the calcium phosphate products. The materials used in Process II may be suitable for making phosphors, but are not economical for making dentifrice polishing agents.

SUMMARY OF THE INVENTION

The present invention provides processes which comprise adding an aqueous phosphoric acid solution to an aqueous slurry of lime with agitation and using sufficient acid to provide an acidic reaction medium. The hydrated DCP or DCPD which is formed is then heated in the reaction medium until it is dehydrated to DCPA. This product may be separated from the reaction medium and used, for example, per se as a dentifrice polishing agent or may be dried to remove surface water or may be stabilized in manners disclosed in the prior art. In accordance with one embodiment of this invention, the resulting DCPA is calcined at temperatures of about 600° to 800° C. to form a CPP containing 70% or more of $\beta$ phase CPP which is suitable as a dentifrice polishing agent in regard to tooth cleaning power, low abrasive properties and fluoride and tin compatibility. Alternatively, the DCPA can be calcined at lower temperatures to form a CPP containing primarily $\gamma$ phase CPP which can be used in phosphor manufacture or as a dental polishing agent.

DETAILED DESCRIPTION OF THE INVENTION

Figure 1:
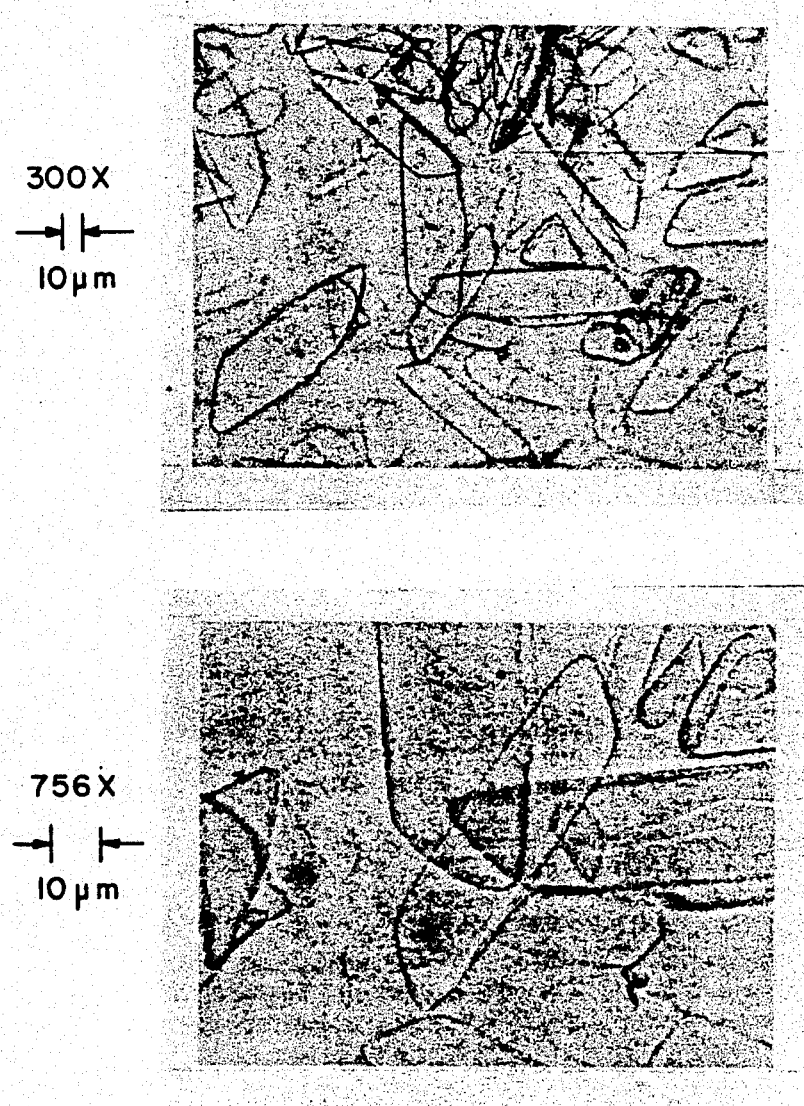
Figure 2:
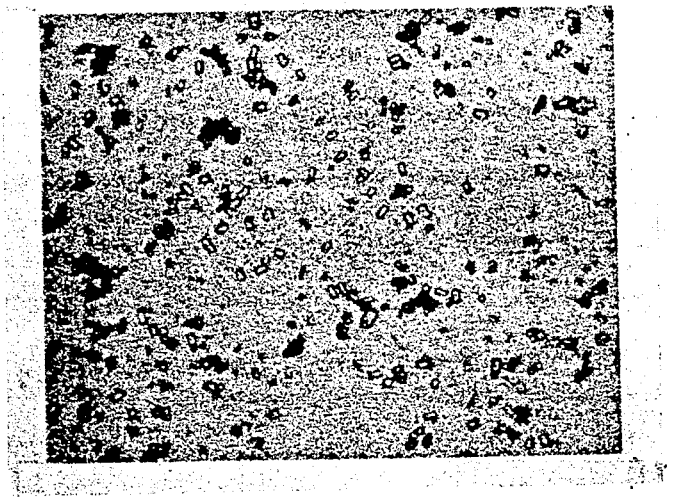
Figure 2:
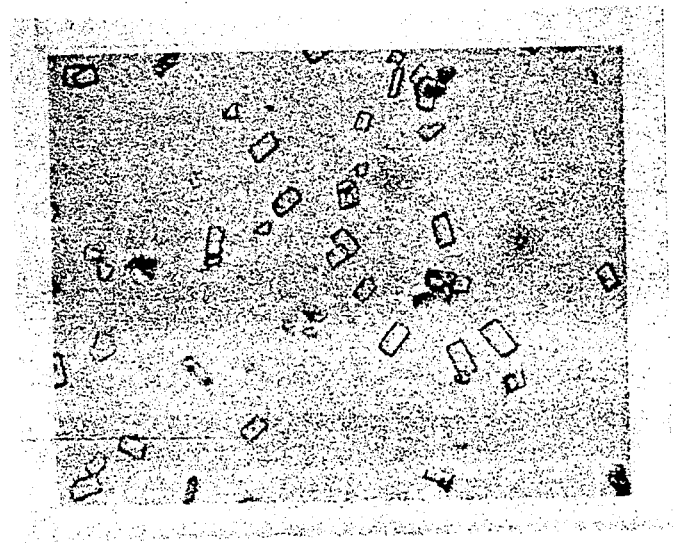
Figure 3:
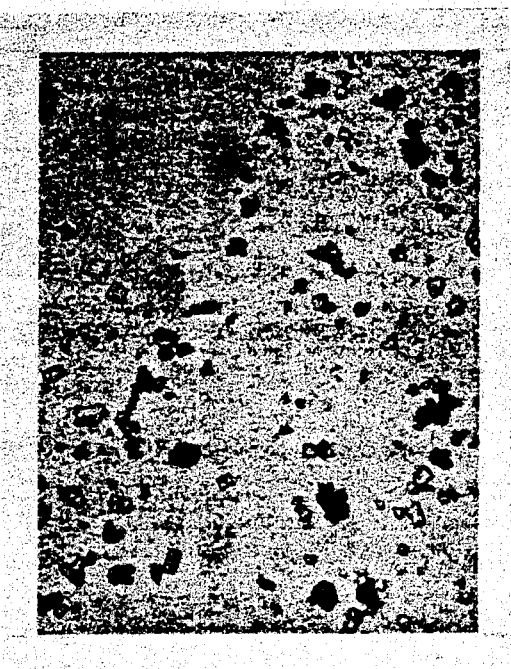

Before describing the present invention in greater detail, attention is called to the accompanying microphotographs, namely:

FIG. 1 which is a microphotograph of hydrated dicalcium phosphate (DCPD) crystals, at 300× and 756× magnification, produced in accordance with one embodiment of the processes of this invention; and, FIG. 2 which is a microphotograph of anhydrous dicalcium phosphate (DCPA) crystals, at 300× and 756× magnification, produced in accordance with one embodiment of this invention from the crystals of FIG. 1; and FIG. 3 which is a microphotograph of $\beta$ calcium pyrophosphate ($\beta$ CPP) crystals, at 756× magnification, produced in accordance with one embodiment of this invention from the crystals of FIG. 2.

Such platelike crystalline dicalcium phosphate dihydrate is identified in the microphotographs of FIG. 1 as having a rhomboid shape, i.e. the crystals are in the shape of parallelogram plates, where the sides of the parallelogram are of unequal lengths. Typically a ratio of side lengths is at least about 2, often up to about 3 or more. The rhomboid has a characteristic acute angle of about 60°. Such platelike crystals can be of substantial size. The surface area of the crystals can be estimated by comparing the dimensions of the crystal viewed in an optical microscope to a reference scale, i.e. such as the 10 micron scale of FIG. 1. Considering only the large opposite flat platelike surfaces such crystals often have a surface area of at least about 2,000 square microns, even up to about 5,000 square microns or higher. Such platelike crystals have a small thickness when compared to the other dimensions so that the ratio of surface area to thickness is at least about 200 and often higher, e.g. at least about 500 and often up to 1,000 or more. Unlike other forms of DCPD, which are generally a mixture of crystals of various habit, such platelike crystals of DCPD also exhibit pearlescence.

In preparing DCPA in accordance with the present invention, the phosphoric acid solution used and the lime slurry to which such solution is added are relatively dilute. Thus, the phosphoric acid solution is about 2.0 to about 6.5 molar $H_3PO_4$ in water, or stated differently should contain about 20% to about 75% by weight of $H_3PO_4$. The solution is preferably substantially free of other compounds. On the other hand, the lime slurry usually contains from about 4 to about 10% by weight of lime, calculated as CaO. The lime used may be in the form of CaO, $Ca(OH)_2$ or mixtures thereof, or their equivalents, but it is preferred to use a lime slurry containing hydrated CaO.

The proportions of $H_3PO_4$ to CaO used are somewhat critical and should provide at least one phosphate ($PO_4^{---}$) radical for each calcium atom with sufficient excess phosphoric acid to provide an aqueous reaction medium having a pH below 5, preferably between about 2.5 and 4.0.

The rate of addition of phosphoric acid solution to lime slurry is also somewhat critical. The acid should not be added too rapidly otherwise there is the possibility that hydrated DCP will be formed containing occluded unreacted lime which will contaminate the DCPA product. A relatively slow rate of addition is beneficial in at least two respects, in that the phosphoric acid added to the lime slurry ordinarily will react completely or substantially completely with the CaO particles and the slurry temperature will be more readily controlled and will not rise too rapidly. For example, during the addition of $H_3PO_4$, it is desirable to maintain the slurry temperature below about 40° C. by cooling, if necessary. Desirable rates of addition are obviously dependent on the $H_3PO_4$ and lime concentrations, but under the preferred concentrations conditions described above generally suitable results can be obtained by continuously adding the $H_3PO_4$ at a constant or somewhat steady (though not constant) rate over a period of about 1.5 to about 3 hours provided adequate agitation is employed. Suitable agitation can be obtained using a turbine type agitator.

In regard to the slurry temperature referred to above, it has been found important to form hydrated DCP at a temperature below 40° C. to form the large plate like crystals shown in FIG. 1. Also, if the hydrated DCP is formed at higher temperatures and subsequently dehydrated to DCPA in the slurry the crystals disintegrate into a fine powder unsuitable for dentifrice use or for subsequent conversion to CPP polishing agent. On the other hand, the crystals formed in accordance with the present process can be dehydrated in the slurry to form crystals such as illustrated in FIG. 2. The crystals represented in FIG. 2 are not only suitable for dentifrice use but can be converted by calcination to a satisfactory CPP of similar crystal structure and useful as a dentifrice polishing agent. A representative crystal structure for such CPP is illustrated in FIG. 3.

After the $H_3PO_4$ has been added to the lime slurry, it is preferred to hold the slurry at a temperature below 40° C. (but above freezing), preferably at 20°-35° C. for a period of about 1 to 4 hours, to permit the substantially complete formation of DCPD crystals, and to permit such crystals to grow to a size such a illustrated in FIG. 1.

After such holding period, the slurry is next heated to cause the hydrated DCP to be converted to DCPA crystals such as illustrated in FIG. 2. The heating is preferably carried out at elevated temperatures, for example, from about 85° to about 100° C.

The conversion of the hydrated DCP to DCPA is accelerated at the higher temperatures and is usually complete within 3 to 4 hours at the higher temperatures. Somewhat longer heating times will be required at lower temperatures. Usually there are two phenomena which signal the completion of conversion of hydrated DCP to DCPA. One of these is a drop in the pH of the slurry by about 0.6 to 1.0 units. The second is a decrease in size of the flat platelets of DCPD. The amount of decrese may vary but is usually on the order of 40 to 60% of the size of DCPD crystals prior to dehydration. In general, the DCPA crystals will have a crystal size, expressed as mass medium diameter, of about 12 to 18 microns.

The DCPA crystals formed are removed from the slurry by filtration, centrifugation or the like and are then dried. Prior to removal, the slurry may be cooled or allowed to cool to a more desirable working temperature, but this is not essential. If the DCPA crystals are to be used as a dentifrice polishing agent they are dried, usually at a moderate temperature such as 90°-110° C., and used as is or may be ground or milled to a somewhat smaller crystal size. If the DCPA crystals are to be converted to CPP they first may be dried in the above manner and then calcined at elevated temperatures or the wet crystals may be subjected to direct calcination. In either case the final CPP products appear to have very similar properties and crystal characteristics.

Calcination of the DCPA is usually carried out at a temperature of about 350° to about 600° C., preferably 450°-575° C., to produce a product which is substantially γ phase CPP, which is also in the form of crystalline flat platelets similar in appearance and size to those of the DCPA crystals. The calcination may be carried out in a rotary calciner or by spreading the DCPA crystals on trays and heating them to the above mentioned temperatures, or they may be calcined in other ways obvious to one skilled in the calcination art. The γ phase product can be used as a dentifrice polishing agent. By the present processes it is possible to produce γ phase CPP having properties suitable as a dentifrice polishing agent in fluoride containing toothpastes as will be described in greater detail in the subsequent disclosure.

On the other hand, if it is desired to produce β phase CPP crystals from the DCPA crystals, the DCPA crystals can be heated in suitable calcining equipment to temperatures in excess of 600° C., for example, from about 625° to about 850° C., preferably 650°-800° C., until the β phase CPP is formed. The resulting product should have at least 70% by weight β phase material but need not be all β phase material for use as a dentifrice polishing agent in toothpaste formulations. In most instances the β phase material produced by the present process will have a dentin abrasion value (RDA) below 750, a tin compatibility above 50%, a sodium fluoride compatibility greater than 80%, a cleaning power in excess of 50 and an RDA to tin compatibility ratio in the range of about 7 to about 12.

In carrying out the conversion of DCPA to either γ phase CPP or β phase CPP by calcination the applicants have found that the dentifrice properties of these CPP materials is influenced by the size of the DCPA batch being calcined. Ordinarily, in working with laboratory or even small pilot plant quantities the DCPA obtained by the present processes can be formed and calcined as previously disclosed herein to provide, on a substantially consistent basis, CPP products having the requisite and desirable properties for dentifrice use. However, if the quantities of DCPA involved are such as are used in commercial operations, it is usually necessary to incorporate in the DCPA alkali metal ions, preferably $Na^+$ ions, prior to calcination to obtain cyrstalline CPP of substantially consistent suitable dentifrice qualities. The amount of such ions can vary substantially, but is desirably, for best results, in the range of about 500 to 2000 ppm, preferably about 800–1800 ppm, based on the DCPA. Such ions can be added to the DCPA after it is formed and removed from the slurry, but are preferably added to the DCPA in the slurry or to the DCPD prior to the formation of the DCPA. Although, many forms of alkali metal compounds can be used to supply the alkali metal ions, they are preferably supplied by the use of alkali metal hydroxides, alkali metal phosphates such as orthophosphates, pyrophosphates, metaphosphates and the like. The preferred alkali metal ion source compounds are sodium hydroxide and tetrasodium pyrophosphate.

The above referred to numerical value characteristics of the β and γ phase CPP of this invention are ascertained by the following test procedures:

The γ and β phase composition of CPP can be determined by x-ray diffraction patterns using techniques described in U.S. Pat. No. 2,876,168 granted Mar. 3, 1959 to Broge et al, the relevant parts of which are hereby incorporated by reference in the present description.

Stannous fluoride compatibility of the γ and β phase CPP materials can be determined according to the following procedure. Ten (10) gram samples of the CPP are shaken for a period of 1 hour with 100 ml portions of a solution containing 250 ppm of fluoride (added as $SnF_2$), and then the mixtures are centrifuged and aliquots are analyzed for fluorine by means of the well known Willard and Winter procedure which includes distillation in the presence of perchloric acid and titration of the distillates against thorium nitrate in the presence of alizarin sulfonate. Hydroxylamine hydrochloride and sodium chloride are added to the distillate before the titrations in accordance with the recommendation in the Analyst 71, 175 (1946). The amount of fluorine remaining in the supernatant is termed "available" fluorine and is expressed as percent of the original fluorine in the solution. Greater fluoride compatibility is indicated by higher percentage values. Monofluophosphate (or MFP) stability is ascertained by the same procedure except that the MFP is hydrolyzed prior to the test to insure that the fluorine therein is released for test purposes.

Radioactive dentin abrasion (RDA) values can be determined by the procedure described in the Journal of Chemical Education Volume 52; No. 4, April, 1975 pages 247–250.

Cleaning power values can be determined in accordance with the procedure described in the Journal of Dental Research, Volume 61, November, 1982, pages 1236–1239.

Stannous compatibility (Sn compatibility) values can be determined in accordance with the procedure described in the above description where reference is made to a published article. The above referenced materials are hereby incorporated by reference in the present description.

The processes of this invention are illustrated by the following specific examples, which are intended to be illustrative but not limitative, parts and percentages being by weight unless otherwise specified.

EXAMPLE 1

A 2.5 gal. (9.5 l) stainless steel reactor equipped with turbine agitator and cooling coils was used. To this was charged 6000 grams of a lime slurry having a temperature of about 25° C. containing 7.23% lime (calculated as CaO). To the lime slurry was added 1817 milliliters of 4.25M $H_3PO_4$ at a rate of 15 ml./min. with agitation and cooling to maintain the temperature of the mixture at about 25° C. After all of the acid had been added the pH of the mixture, (which was now primarily DCPD in water) was about 3.5. The mixture was held at this temperature and pH for about 1.5 hours, after which the temperature was increased to 90°–95° C. and held at that temperature for 2 hours. The product in the mixture was about 90% anhydrous DCP, and was separated from the liquid by filtration, was washed and then air dried. This product was composed primarily of small sized crystals (68%+20 microns) such as are illustrated in FIG. 2. This material is hereafter referred to as Product A.

A part (300 grams) of Product A was calcined in an oven heated, flighted laboratory calciner at a heating rate of about 5.1° C./min. to a final temperature of about 680° C. When this temperature was reached the calciner was cooled (while rotating continuously) to approximately 200° C. over a period of about 90 minutes prior to removal from the oven. The cooled product taken from the calciner, hereafter referred to as Product B, was primarily β phase CPP and had the following characteristics:

| | |
|---|---|
| β Phase CPP | <70% |
| Stannous compatibility (SnC) | 81 |
| Sodium Fluoride compatibility | 91 |
| Particle Size (+20 microns) | 70.6% |
| RDA | 726 |
| RDA/SnC ratio | 8.9 |

The sodium fluoride compatibility value was based on accelerated aging at 60° C. for 5 days.

EXAMPLE 2

A lime slurry (13.5% CaO content in water) which had been aged for about 14 days was charged to a 10 gallon (37.8 l) jacketed tank reactor provided with agitation. This slurry was diluted with tap water until the resultant slurry contained about 7.5% CaO—at which point it occupied about 30% of the tank volume. Phosphoric acid of 34% concentration was added slowly and continuously to the lime slurry over a period of about 2 hours with good agitation (about 350 rpm) while maintaining the slurry temperature below 30° C. The agitator speed was increased to about 450 rpm when the pH of the slurry decreased to 10., The acid addition was continued until the slurry pH dropped to pH 3.5 and remained there after sufficient time to allow for upward pH drift. Next 50% NaOH solution, (about 132 grams) was added to raise the pH to 4.5. The resulting slurry was then divided into 3 equal parts and each part was subjected to milling for 15 minutes in a Sweco vibro-energy type mill of 2.6 gal. (9.8 l) working capacity charged with about 190 pounds (86.2 kg) of $\frac{1}{2}$ inch (1.3 cm) sintered alumina grinding cylinders. The three parts of slurry, now containing milled DCPD particles, were returned to the tank reactor and heated up to about 95° C., which required about 30 minutes. The slurry was held at that temperature for about 1 hour and then cooled to 40° C. using cooling water in the tank jackets, after which 20 grams of tetrasodium pyrophosphate were added and the slurry was agitated for about 45 minutes. Next the slurry, which now contained substantially DCPA, was filtered through a Buchner funnel to provide 3 filter cakes of DCPA of about 40% moisture content each. The cakes were then dried for about 48 hours at 50° C. in a forced air oven and then the dried DCPA was milled in a 3.5 gal. (13.2 l) jar mill with 13/16 inch (2.1 cm) Burrundum grinding cylinders for about 3 hours using a DCPA loading of 2000 grams, with a 1:5.66 weight ratio of DCPA to grinding cylinders.

The dry, ground DCPA in amount of 3500 grams was next charged to an INCOLOY 800 and INCONEL 600 calciner 8.75 inches (22.2 cm) in diameter and 20.75 inches (52.7 cm) long, without flights. The calciner was positioned in a Blue M Model 86 55F-3 furnace with a Honeywell automatic temperature programmer. The calciner was then started rotating at 22 rpm and the contents heated at the rate of 4.5°-5° C./min. until a temperature of 640° C. was attained. The contents were then maintained at that temperature for 30 minutes after which the oven heater was cut off and the door opened and the calciner and contents cooled overnight to 200° C. The resultant product, which was primarily β phase CPP, contained about 1241 ppm of Na+ on a DCPD basis. This product, hereafter Product C, had the following characteristics:

| % β phase | 84 |
| % Sn compatibility | 59 |
| % SnF$_2$ compatibility | 94 |
| % Na fluoride compatibility | 84 |
| RDA | 567 |
| RDA/tin compatibility | 9.6 |

EXAMPLE 3

The procedure of Example 2 was repeated with the following exceptions:

(a) The concentration of CaO in the lime slurry prior to phosphoric acid addition was 6%.

(b) The phosphoric acid concentration was 75%.

(c) No NaOH solution was added to the slurry and the pH of the slurry was allowed to remain at 3.5.

(d) Fifty grams of tetrasodium pyrophosphate (rather than 20 grams) were added to the DCPA slurry prior to filtration.

(e) The dry ground DCPA was calcined until a temperature of 660° C. was attained and the contents of the calciner were maintained at that temperature for 2 hours.

The product of this procedure, hereafter Product D, contained primarily β phase CCP and about 950 ppm of Na+ on a DCPD basis. This product also had the following characteristics:

| % β phase | 76 |
| % Sn compatibility | 62 |
| % SnF$_2$ compatibility | 82 |
| Na fluoride compatibility | 76 |
| RDA | 577 |
| RDA/Sn compatibility | 9.3 |

EXAMPLE 4

A part (300) grams of Product A, as produced in Example 1, was calcined in an oven heated, flighted laboratory calciner at a heating rate of about 5.1° C./min. to a final temperature of about 550° C. When this temperature was reached the calciner was cooled (while rotating continuously) to approximately 200° C. over a period of about 90 minutes prior to removal from the oven. The cooled product taken from the calciner is hereafter referred to as Product E.

EXAMPLE 5

The dentifrice polishing agent, Product B (Example 1) can be used by incorporating this product in toothpaste formulations containing the ingredients in the proportions set forth in Table I.

EXAMPLE 6

The dentifrice polishing agent, Product C (Example 2) can be used by incorporating this product in toothpaste formulations containing the ingredients in the proportion set forth in Table I.

TABLE I

| | Formulation Number | | | |
|---|---|---|---|---|
| | 1 | 2 | 3 | 4 |
| Product B | 30 | 30 | — | — |
| Product C | — | — | 30 | 30 |
| Glycerine | 35 | 35 | 35 | 35 |
| Sodium Benzoate | 0.5 | 0.5 | 0.5 | 0.5 |
| Sodium Lauryl Sulfate | 1.5 | 1.5 | 1.5 | 1.5 |
| Carboxy Methyl Cellulose | 0.75 | 0.75 | 1.75 | 1.75 |
| Water | 32.03 | 30.85 | 31.03 | 29.85 |
| NaF | 0.22 | — | 0.22 | — |
| SnF$_2$ | — | 0.4 | — | 0.4 |
| Sn$_2$P$_2$O$_7$ | — | — | — | 1.0 |
| | 100.00 | 100.00 | 100.00 | 100.00 |

EXAMPLE 7

The dentifrice polishing agents, Product D (Example 3) and Product E (Example 4) can be used by incorporating these products in toothpaste formulations containing the ingredients in the proportions set forth in Table II.

TABLE II

| | Formulation Number | | | |
|---|---|---|---|---|
| | 5 | 6 | 7 | 8 |
| Product D | 30 | 30 | — | — |
| Product E | — | — | 30 | 30 |
| Glycerine | 35 | 35 | 35 | 35 |
| Sodium Benzoate | 0.5 | 0.5 | 0.5 | 0.5 |
| Sodium Lauryl Sulfate | 1.5 | 1.5 | 1.5 | 1.5 |
| Carboxy Methyl Cellulose | 1.75 | 1.75 | 0.75 | 0.75 |
| Water | 31.03 | 29.85 | 31.49 | 32.03 |
| NaF | 0.22 | — | — | 0.22 |
| $SnF_2$ | — | 0.4 | — | — |
| $Sn_2P_2O_7$ | — | 1.0 | — | — |
| MFP | — | — | 0.76 | — |
| | 100.00 | 100.00 | 100.00 | 100.00 |

The dentifrice formulations of this invention may contain a large variety of ingredients in addition to the polishing agents illustrated in the above Examples, and in addition to or as substitutes for the other ingredients set forth in the above Examples. Moreover, the formulations can be in liquid, paste or powder form. As examples of such additional or substitute ingredients may be mentioned humectants such as sorbitol, glycerine and the like; sweeteners such as sugars, saccharin, aspartame and the like; detergents or sudsing agents such as alkyl sulfate like sodium lauryl sulfate, surface active condensation products of ethylene oxide and alcohols such as tridecanol, dodecanol, etc., and, sucrose, monolaurate and the like; so called binding agents such as hydroxy ethyl cellulose, sodium carboxy methyl cellulose and the like; and coloring agents and flavors. The liquids and pastes usually differ from the powders in that they contain water while the powders do not. Of course, other ingredients not harmful to the use of the dentifrice may be employed.

Usually, the dentifrice formulations have a pH in water between about 3 and 7, with a pH of about 3.5 to about 5 being preferred if stannous ion is present. Such formulations, while they contain a fluoride such as NaF, MFP or $SnF_2$ or the like, have a fluoride concentration such that the fluorine compound provides about 100 to 4,000 ppm, preferably about 500-2000 ppm of available fluoride ions.

The fluoride source in the dentifrice formulations or compositions can be derived from any organic or inorganic fluorine or fluoride compound capable of releasing available fluorine during use. However, the fluorides used are preferably inorganic fluorides and more preferably NaF, MFP or $SnF_2$.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A process for producing crystalline platelets of anhydrous dicalcium phosphate which comprises adding an aqueous solution of phosphoric acid to an aqueous slurry of lime particles in proportions to provide a final pH below 5 and a calcium to $PO_4$ ratio of about 1:1 and at a rate sufficient to enable a substantially complete reaction of said acid and lime particles while maintaining the temperature sufficiently low to form a slurry of dicalcium phosphate dihydrate particles and then heating said latter slurry at a temperature and for a period of time sufficient to convert said dihydrate particles to crystalline platelets of anhydrous dicalcium phosphate having a mass medium diameter of about 12 to 18 microns.

2. A process for producing platelike crystalline dicalcium phosphate dihydrate comprising adding phosphoric acid to an aqueous slurry of lime.

3. The process of claim 2 wherein said adding is at a temperature no higher than about 40° C.

4. The process of claim 3 wherein said phosphoric acid is a solution of about 20 to about 75 percent by weight of phosphoric acid.

5. The process of claim 4 wherein said slurry comprises up to about 10 percent by weight calcium oxide.

6. The process of claim 3 wherein after substantially complete reaction of said acid and said lime there is provided an aqueous reaction medium having a pH below about 5.

7. The process of claim 6 wherein said pH is between about 2.5 and 4.0.

8. The process of claim 6 wherein said medium is held at a temperature between about 20° to 35° C. for at least one hour.

9. Plate-like crystalline dicalcium phosphate dihydrate produced by the addition of an aqueous phosphoric acid solution to an aqueous slurry of lime wherein sufficient acid is employed to provide an acidic reaction medium.

10. Dihydrate of claim 9 having a rhomboid shape with a ratio of side lengths of at least about 2.

11. Dihydrate of claim 10 wherein said rhomboid has an acute angle of about 60°.

12. Dihydrate of claim 9 exhibiting pearlescence.

13. Dihydrate of claim 9 having a surface area as determined by optical microscope of at least about 2000 square microns.

14. Dihydrate of claim 13 having a ratio of surface area to thickness of at least about 200.

15. Dihydrate of claim 9 wherein said phosphoric acid comprises a solution of about 20 to about 75 percent by weight of phosphoric acid.

16. Dihydrate of claim 15 wherein said slurry comprises from about 4 to about 10 percent by weight calcium oxide.

17. Dihydrate of claim 9 wherein said adding is at a temperature no higher than about 40° C.

18. Dihydrate of claim 17 wherein the adding of said phosphoric acid solution to said aqueous slurry of lime results in an aqueous medium having a pH less than about 5.

19. Dihydrate of claim 18 wherein said pH is between about 2.5 and 4.0.

20. Dicalcium phosphate dihydrate comprising substantially uniform platelike crystals, said crystals having a ratio of surface area to thickness of at least about 200.

21. Dihydrate of claim 20 exhibiting pearlescence.

22. Dihydrate of claim 20 having a rhomboid shape with a ratio of side lengths of at least about 2.

23. Dihydrate of claim 22 wherein said rhomboid has an angle of about 60°.

24. Dihydrate of claim 20 having a surface area as determined by optical microscope of at least about 2000 square microns.

25. Platelike rhomboid-shaped anhydrous dicalcium phosphate converted from platelike rhomboid-shaped dicalcium phosphate dihydrate of claim 1.

26. Phosphate of claim 25 comprising crystals having a major length of at least about 30 microns.

27. Platelike rhomboid-shaped calcium pyrophosphate converted from platelike rhomboid-shaped dicalcium phosphate dihydrate of claim 25.

28. Pyrophosphate of claim 27 having a particle size of at least about 20 microns.

29. A dentifrice composition comprising a fluorine source and a polishing agent comprising substantially uniform crystalline platelets of anhydrous dicalcium phosphate derived from a dihydrate produced by the addition of an aqueous phosphoric acid solution to an aqueous slurry of lime.

30. The dentifrice composition as in claim 29 wherein the fluorine source is monofluorophosphate.

31. A dentifrice composition comprising a fluorine source and a polishing agent comprising substantially uniform crystalline platelets of $\beta$ phase calcium pyrophosphate derived by calcining dehydrated crystals of dicalcium phosphate dihydrate produced by the addition of an aqueous phosphoric acid solution to an aqueous slurry of lime.

32. The dentifrice composition according to claim 31 wherein the fluorine source is selected from NaF, monofluorophosphate and stannous fluoride.

33. The dentifrice composition of claim 31 wherein the fluorine source is selected from the group consisting of sodium fluoride, monofluorophosphate and stannous fluoride and wherein from 800 to 1800 ppm of sodium ions are incorporated in the dicalcium phosphate prior to calcination by the addition of sodium hydroxide or tetrasodium pyrophosphate.

34. The dentifrice composition of claim 33 wherein the fluorine source is NaF.

35. The dentifrice composition of claim 33 wherein the fluorine source is stannous fluoride.

36. The dentifrice composition of claim 33 wherein the fluorine source provides about 500–2000 ppm of available fluoride ions.

37. A dentifrice composition comprising a fluorine source selected from the group consisting of NaF, monofluorophosphate or stannous fluoride and a polishing agent comprising $\beta$ phase calcium pyrophosphate produced in accordance with the process which comprises calcining an anhydrous dicalcium phosphate, produced in accordance with the process of claim 1 at a temperature in excess of 600° C. until calcium pyrophosphate particles composed predominantly of $\beta$ phase particles and a mass medium diameter of 12–18 microns are produced.

* * * * *